US006713119B2

(12) United States Patent
Hossainy et al.

(10) Patent No.: US 6,713,119 B2
(45) Date of Patent: Mar. 30, 2004

(54) BIOCOMPATIBLE COATING FOR A PROSTHESIS AND A METHOD OF FORMING THE SAME

(75) Inventors: Syed F. A. Hossainy, Fremont, CA (US); Deborra Sanders-Millare, San Jose, CA (US); Judy A. Guruwaiya, San Jose, CA (US); Daniel A. Castro, Santa Clara, CA (US); Sameer Harish, Fremont, CA (US); Steven Z. Wu, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/470,559

(22) Filed: Dec. 23, 1999

(65) Prior Publication Data

US 2002/0193475 A1 Dec. 19, 2002

Related U.S. Application Data

(63) Continuation-in-part of application No. 09/390,855, filed on Sep. 3, 1999, now Pat. No. 6,287,628, and a continuation-in-part of application No. 09/390,069, filed on Sep. 3, 1999, now Pat. No. 6,379,381.

(51) Int. Cl.$^7$ ................................. A61F 2/02

(52) U.S. Cl. ...................... 427/2.25; 427/2.1; 427/2.14; 427/2.24; 427/2.21; 524/503; 525/56; 525/57; 623/1.2; 623/1.11; 623/1.12; 623/1.34; 623/1.42; 623/1.43; 623/1.46

(58) Field of Search ................................ 427/2.1, 2.14, 427/2.24, 2.25, 2.21; 523/105, 112, 113; 524/113, 173, 315, 379, 503; 525/56, 57; 623/1.2, 1.12, 1.11, 1.34, 1.42, 1.43, 1.46

(56) References Cited

U.S. PATENT DOCUMENTS

| | | | |
|---|---|---|---|
| 2,072,303 A | 3/1937 | Herrmann et al. ........ | 128/335.5 |
| 4,733,665 A | 3/1988 | Palmaz ........................ | 128/343 |
| 4,800,882 A | 1/1989 | Gianturco .................... | 128/343 |
| 4,886,062 A | 12/1989 | Wiktor ........................ | 128/343 |
| 4,977,901 A | * 12/1990 | Ofstead ....................... | 128/772 |
| 5,328,471 A | 7/1994 | Slepian ........................ | 604/101 |
| 5,464,650 A | 11/1995 | Berg et al. .................... | 427/2.3 |
| 5,578,073 A | 11/1996 | Haimovich et al. ............ | 623/1 |
| 5,605,696 A | 2/1997 | Eury et al. .................... | 424/423 |
| 5,628,730 A | 5/1997 | Shapland et al. .............. | 604/21 |
| 5,667,767 A | 9/1997 | Greff et al. ............... | 424/9.411 |
| 5,670,558 A | 9/1997 | Onishi et al. ................. | 523/112 |
| 5,700,286 A | 12/1997 | Tartaglia et al. ................ | 623/1 |
| 5,716,981 A | 2/1998 | Hunter et al. ................ | 514/449 |
| 5,800,392 A | 9/1998 | Racchini ...................... | 604/96 |
| 5,824,049 A | 10/1998 | Ragheb et al. ................. | 623/1 |
| 5,830,178 A | 11/1998 | Jones et al. .................... | 604/49 |
| 5,837,313 A | 11/1998 | Ding et al. ................. | 427/2.21 |

(List continued on next page.)

FOREIGN PATENT DOCUMENTS

| | | |
|---|---|---|
| EP | 0 310 856 | 2/1989 |
| EP | 665023 A1 * | 8/1995 |
| WO | WO 91/12846 | 9/1991 |
| WO | WO 96/40174 | 12/1996 |
| WO | WO 97/45105 | 12/1997 |
| WO | WO 99/01118 | 1/1999 |
| WO | WO 99/63981 | 12/1999 |
| WO | WO 00/02599 | 1/2000 |
| WO | WO 00/12147 | 3/2000 |
| WO | WO 00/64506 | 11/2000 |

OTHER PUBLICATIONS

Barath et al.; *Low Dose of Antitumor Agents Prevents Smooth Muscle Cell Proliferation After Endothelial Injury*; JACC vol. 13, No. 2: Feb. 1989:252A (Abstract).

Miyazaki et al., "*Antitumor Effect of Implanted Ethylene–Vinyl Alcohol Copolymer Matrices Containing Anticancer Agents on Ehrlich Ascites Carcinoma and P388 Leukemia in Mice*," Chem. Pharm. Bull. 33(6) (1985), pp. 2490–2498.

Shigeno, *Prevention of Cerebrovascular Spasm By Bosentan, Novel Endothelin Receptor*; Chemical Abstract 125:212307 (1996).

Shozo Miyazaki et al., "Antitumor Effect of Implanted Ethylene–Vinyl Alcohol Copolymer Matrices Containing Anticancer Agents on Ehrlich Ascites Carcinoma and P388 Leukemia in Mice," Chem. Pharm. Bull, vol. 33(6), pp. 2490–2498 (1985).

Yuji Matsumaru et al., "Embolic materials for endovascular treatment of cerebral lesions," J. Biomater. Sci. Polymer Edn, vol. 8, No. 7, pp. 555–569 (1997).

Hidefumi Ohsawa, MD, et al., "Preventive effects of an antiallergic drug, pemirolast potassium, on restenosis after percutaneous transluminal coronary angioplasty," American Heart Journal, vol. 136(6) pp. 1081–1087 (Dec. 1998).

Norio Miyazawa et al., "Effects of Pemirolast and Tranilast on Intimal Thickening After Arterial Injury in the Rat," Journal of Cardiovascular Pharmacology™, pp. 157–162, Received Dec. 9, 1996, revision accepted Mar. 4, 1997. © 1997.

*Primary Examiner*—Judy M. Reddick
(74) *Attorney, Agent, or Firm*—Cameron K. Kerrigan

(57) ABSTRACT

A coating for a prosthesis, for example a stent, and a composition for forming the coating is disclosed. The coating can serve as a primer, allowing substances, such as polymers, to be effectively secured by the prosthesis. Alternatively, the coating can serve as a reservoir, allowing for the local and sustained release of a therapeutic substance to biological tissues. The composition can be formed from an ethylene vinyl alcohol copolymer and a dimethylsulfoxide solvent, with or without a therapeutic substance. Alternatively, the composition can be formed from an ethylene vinyl alcohol copolymer, a dimethylsulfoxide solvent, and a wetting fluid, with or without a therapeutic substance. The composition is applied to a surface of the prosthesis and essentially all of the dimethylsulfoxide solvent or dimethylsulfoxide solvent/wetting fluid is removed or allowed to evaporate to form the coating.

29 Claims, 1 Drawing Sheet

U.S. PATENT DOCUMENTS

| | | | |
|---|---|---|---|
| 5,851,508 A | 12/1998 | Greff et al. | 424/9.411 |
| 5,865,814 A | 2/1999 | Tuch | 604/265 |
| 5,873,904 A | 2/1999 | Ragheb et al. | 623/1 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,010,530 A | 1/2000 | Goicoechea | 623/1 |
| 6,015,541 A | 1/2000 | Greff et al. | 424/1.25 |
| 6,096,070 A | 8/2000 | Ragheb et al. | 623/1 |
| 6,153,252 A | 11/2000 | Hossainy et al. | 427/2.3 |
| 6,165,212 A | 12/2000 | Dereume et al. | 623/1.13 |
| 6,258,121 B1 | 7/2001 | Yang et al. | 623/1.46 |

\* cited by examiner

BIOCOMPATIBLE COATING FOR A PROSTHESIS AND A METHOD OF FORMING THE SAME

CROSS REFERENCE

This application is a continuation-in-part of application Ser. No. 09/390,855, filed Sep. 3, 1999 now U.S. Pat. No. 6,287,628; this application is also a continuation-in-part of application Ser. No. 09/390,069, filed Sep. 3, 1999 now U.S. Pat. No. 6,719,381.

BACKGROUND OF THE INVENTION

1. Field of the Invention

This invention relates to a coating for implantable devices, such as an expandable intraluminal prosthesis, one example of which includes a stent. Moreover, the invention is directed to a composition for coating an implantable device.

2. Description of the Related Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an expandable intraluminal prosthesis, one example of which includes a stent, is implanted in the lumen to maintain the vascular patency. Stents are scaffoldings, usually cylindrical or tubular in shape, which function to physically hold open and, if desired, to expand the wall of the passageway. Typically stents are capable of being compressed, so that they can be inserted through small cavities via small catheters, and then expanded to a larger diameter once they are at the desired location. Examples in patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

In treating the damaged vasculature tissue and to further fight against thrombosis and restenosis, there is a need for administrating therapeutic substances to the treatment site. For example, anticoagulants, antiplatelets and cytostatic agents are commonly used to prevent thrombosis of the coronary lumen, to inhibit development of restenosis, and to reduce post-angioplasty proliferation of the vascular tissue, respectively. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more effective results.

One commonly applied technique for the local delivery of a drug is through the use of medicated stents. One proposed method provided stents which were seeded with endothelial cells (Dichek, D. A. et al. Seeding of Intravascular Stents With Genetically Engineered Endothelial Cells; Circulation 1989; 80: 1347–1353). Briefly, endothelial cells were seeded onto stainless steel stents and grown until the stents were covered. The cells were therefore able to be delivered to the vascular wall where they provided therapeutic proteins. Another proposed method of providing a therapeutic substance to the vascular wall included use of a heparin-coated metallic stent, whereby a heparin coating was ionically or covalently bonded to the stent. Significant disadvantages associated with the aforementioned methods include significant loss of the therapeutic substance from the body of the stent during delivery and expansion of the stent, and an absolute lack of control of the release rate of the therapeutic substance from the stent.

Another proposed method involved the use of a polymeric carrier coated onto the surface of a stent, as disclosed in U.S. Pat. No. 5,464,650 issued to Berg et al. Berg disclosed applying to a stent body a solution which included a specified solvent, a specified polymer dissolved in the solvent, and a therapeutic substance dispersed in the blend. The solvent was allowed to evaporate, leaving on the stent surface a coating of the polymer and the therapeutic substance impregnated in the polymer. Among the specified, suitable choices of polymers listed by Berg, empirical results were specifically provided for poly(caprolactone) and poly (L-lactic acid). The preferred choice of mutually compatible solvents included acetone or chloroform. As indicated by Berg, stents where immersed in the solution 12 to 15 times or sprayed 20 times. The evaporation of the solvent provided a white coating. A white coloration is generally indicative of a brittle polymeric coating. A brittle polymeric coating is an undesirable characteristic, since portions of the coating typically become detached during stent expansion. Detachment of the coating causes the quantity of the therapeutic substance to fall below a threshold level sufficient for the effective treatment of a patient.

Accordingly, it is desirable to provide an improved coating that is susceptible to expanding with a prosthesis without significant detachment from the surface of the prosthesis. It is also desirable for the polymer to be able to strongly adhere to the surface of the prosthesis, thereby preventing loss of the polymeric coating during prosthesis delivery. Other desirable features include, but are not limited to, a polymeric coating which allows for a significant control of the release rate of a therapeutic substance, a polymeric coating that can serve as an under-layer for substances which do not easily or effectively bind or adhere to the surface of the prosthesis, a polymeric solution which need not be applied excessively to the surface of the prosthesis to form a coating of a suitable thickness, and a polymeric solution that can be uniformly applied to the surface of the prosthesis.

SUMMARY OF THE INVENTION

In accordance with one embodiment of the present invention, a method for forming a coating onto a surface of a prosthesis, e.g., a stent, is provided. In one embodiment, the method comprises applying to the surface of the prosthesis a composition which includes an ethylene vinyl alcohol copolymer and a dimethylsulfoxide solution. The ethylene vinyl alcohol copolymer can constitute from about 0.1% to about 35%, usefully from about 12% to about 20% by weight of the total weight of the composition and the dimethylsulfoxide solution can constitute from about 65% to about 99.9%, usefully from about 80% to about 88% by weight of the total weight of the composition.

In accordance with another embodiment, a fluid can be added to the composition which can enhance the wetting of the composition. To enhance the wetting of the composition, a suitable fluid typically has a high capillary permeation. A suitably high capillary permeation corresponds to a contact angle less than about 90°. The wetting fluid can have a viscosity not greater than about 50 centipoise. The wetting fluid, accordingly, when added to the composition, reduces the viscosity of the composition. The wetting fluid should be mutually compatible with the ethylene vinyl alcohol copolymer and dimethylsulfoxide solution and should not precipitate the copolymer. Useful examples of the wetting fluid include, but are not limited to, tetrahydrofuran (THF), dimethylformamide (DMF), 1-butanol, n-butyl acetate, and mixtures thereof. In this embodiment, the ethylene vinyl alcohol copolymer can constitute from about 0.1% to about 35%, usefully from about 10% to about 25% by weight of the total weight of the composition, the dimethylsulfoxide can constitute from about 19.9% to about 98.9%, usefully from about 50% to about 79% by weight of the total weight of the composition, the wetting fluid can constitute from about 1% to about 80%, usefully from about 5% to about 40% by weight of the total weight of the composition.

In accordance with another embodiment, sufficient amounts of a therapeutic substance or a combination of substances are dispersed in the blended composition of the ethylene vinyl alcohol copolymer and the dimethylsulfoxide solution. In this embodiment, the ethylene vinyl alcohol copolymer can constitute from about 0.1% to about 35%, usefully from about 12% to about 20% by weight of the total weight of the composition, the dimethylsulfoxide solution can constitute from about 59.9% to about 99.8%, usefully from about 79% to about 87% by weight of the total weight of the composition, and the therapeutic substance can constitute from about 0.1% to about 40%, usefully from about 1% to about 9% by weight of the total weight of the composition.

In accordance with another embodiment, sufficient amounts of a therapeutic substance or combination of substances are dispersed in the blended composition of the ethylene vinyl alcohol copolymer, the dimethylsulfoxide solution, and a wetting fluid. In this embodiment, the ethylene vinyl alcohol copolymer can constitute from about 0.1% to about 35%, usefully from about 10% to about 25% by weight of the total weight of the composition, the dimethylsulfoxide solution can constitute from about 19.8% to about 98.8%, usefully from about 49% to about 79% by weight of the total weight of the composition, the wetting fluid can constitute from about 1% to about 80%, usefully from about 5% to about 40% by weight of the total weight of the composition, and the therapeutic substance can constitute from about 0.1% to about 40%, usefully from about 1% to about 9% by weight of the total weight of the composition.

The composition can be applied to the prosthesis simply by immersing the prosthesis into the composition or by spraying the composition onto the surface of the prosthesis. The dimethylsulfoxide solution or the combination of the dimethylsulfoxide solution and wetting fluid is removed from the composition which is applied to the surface of the prosthesis. The copolymer, with or without the therapeutic substance, solidifies and adheres to the surface of the prosthesis. One technique for removing the dimethylsulfoxide solution or combination of the dimethylsulfoxide solution and wetting fluid includes allowing the components to evaporate to a substantial elimination, for example, by heating the prosthesis at a predetermined temperature for a predetermined duration of time.

In accordance with another embodiment, a layer comprising a polymeric material, without a therapeutic substance, can be formed on the therapeutic substance impregnated ethylene vinyl alcohol coating. The layer can be any suitable polymeric material, including an ethylene vinyl alcohol copolymer. The layer provides a rate reducing membrane for therapeutic substances that may be quickly released from the coating.

In accordance with another embodiment of the invention a coating for a prosthesis is provided. In one embodiment, the coating comprises an ethylene vinyl alcohol copolymer. The ethylene vinyl alcohol copolymer can serve as a primer, allowing substances, such as a variety of biocompatible polymers, to be effectively secured by the prosthesis.

In accordance to another embodiment, the coating comprises an ethylene vinyl alcohol copolymer and a therapeutic substance carried by the copolymer. The coating allows the therapeutic substance to be retained onto the prosthesis during delivery and, if applicable, expansion and also allows for a sustained release of the substance at the site of implantation. Therapeutic substances such as antineoplastics, antiinflammatories, antiplatelets, anticoagulants, antifibrins, antithrombins, antimitotics, antiproliferatives, antibiotics, antioxidants, antiallergics, and combinations thereof can be carried by the copolymer.

DETAILED DESCRIPTION OF THE EMBODIMENTS

Composition

The embodiments of the composition are prepared by conventional methods wherein all components are combined, then blended. More particularly, in accordance to one embodiment, a predetermined amount of an ethylene vinyl alcohol copolymer (commonly known by the generic name EVOH or by the trade name EVAL) is added to a predetermined amount of a dimethylsulfoxide (DMSO) solvent at ambient pressure and under anhydrous atmosphere. If necessary, gentle heating and stirring and/or mixing can be employed to effect dissolution of the copolymer into the DMSO solvent, for example 12 hours in a water bath at about 60° C.

Ethylene vinyl alcohol copolymer refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 44%. Typically, 44 mole percent ethylene is suitable. As a general rule, an increase in the amount of the ethylene comonomer content decreases the rate that a therapeutic substance is released from the matrices of the copolymer. The release rate of a therapeutic substance decreases as the hydrophilicity of the polymer decreases. An increase in the amount of the ethylene comonomer content decreases the hydrophilic nature of vinyl alcohol comonomer. Ethylene vinyl alcohol copolymers are available commercially from companies such as Aldrich Chemical Company, Milwaukee, Wis., or EVAL Company of America, Lisle, Ill., or can be prepared by conventional polymerization procedures that are well known to one of ordinary skill in the art. Typically, the ethylene vinyl alcohol copolymer can comprise from about 0.1% to about 35%, usefully from about 12% to about 20% by weight of the total weight of the composition. Typically, the DMSO solvent can comprise from about 65% to about 99.9%, usefully from about 80% to about 88% by weight of the total weight of the composition. A specific weight ratio is dependent on factors such as the material from which the prosthesis is made and the geometrical structure of the prosthesis.

Figure 1A:
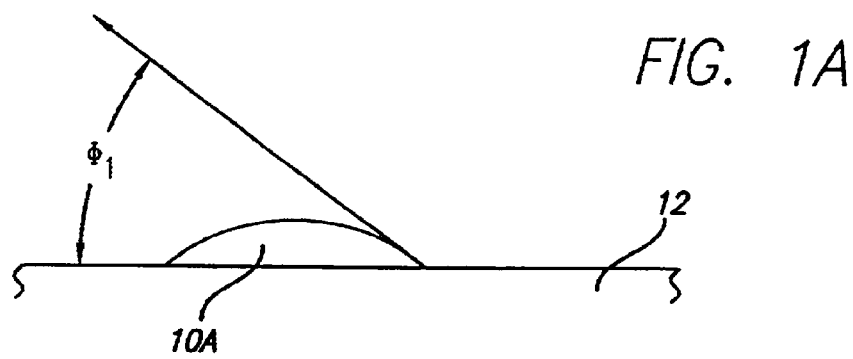
FIG. 1A illustrates a fluid on a solid substrate having a contact angle $\Phi_1$.
Figure 1B:
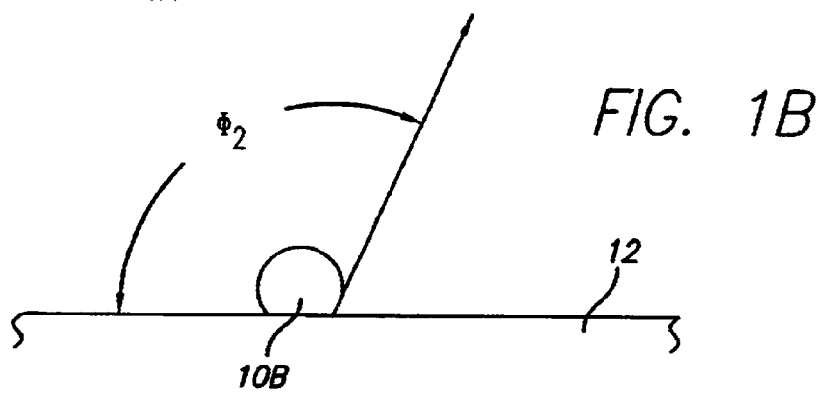
FIG. 1B illustrates a fluid on a solid substrate having a contact angle $\Phi_2$.

In accordance with another embodiment, a fluid can be added to the composition which can enhance the wetting of the composition. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 1A illustrates a fluid droplet 10A on a solid substrate 12, for example a stainless steel surface. Fluid droplet 10A has a high capillary permeation that corresponds to a contact angle $\Phi_1$, which is less than about 90°. In contrast, FIG. 1B illustrates a fluid droplet 10B on solid substrate 12, having a low capillary permeation that corresponds to a contact angle $\Phi_2$, which is greater than about 90°. The wetting fluid, typically, should have a viscosity not greater than about 50 centipoise, usefully about 0.3 to about 5 centipoise, more usefully about 0.4 to about 2.5 centipoise. The wetting fluid, accordingly, when added to the composition, reduces the viscosity of composition. The wetting fluid should be mutually compatible with the ethylene vinyl alcohol copolymer and DMSO solvent and should not precipitate the copolymer. Useful examples of the wetting fluid include, but are not limited to, tetrahydrofuran (THF), dimethylformamide (DMF), 1-butanol, n-butyl acetate, and mixtures and combinations thereof. In this embodiment, the ethylene vinyl alcohol copolymer can comprise from about 0.1% to about 35%, usefully from about 10% to about 25% by weight of the total weight of the composition. The DMSO solvent can comprise from about 19.9% to about 98.9%, usefully from about 50% to about 79% by weight of the total weight of the composition. The wetting fluid can comprise from about 1% to about 80%, usefully from about 5% to about 40% by weight of the total weight of the composition. The specific weight ratio of the wetting fluid depends on the type of wetting fluid employed and the weight ratio of the ethylene vinyl alcohol copolymer and the DMSO solvent. More particularly, tetrahydrofuran used as the wetting fluid can comprise from about 1% to about 44%, usefully about 21% by weight of the total weight of the solution. Dimethylformamide used as the wetting fluid can comprise from about 1% to about 80%, usefully about 8% by weight of the total weight of the solution. 1-butanol used as the wetting fluid can comprise from about 1% to about 33%, usefully about 9% by weight of the total weight of the solution. N-butyl acetate used as the wetting fluid can comprise from about 1% to about 34%, usefully about 14% by weight of the total weight of the solution.

In accordance with another embodiment, sufficient amounts of a therapeutic substance or a combination of substances are dispersed in the blended composition of the ethylene vinyl alcohol copolymer and the DMSO solvent, without the wetting fluid. In this embodiment, the ethylene vinyl alcohol copolymer can comprise from about 0.1% to about 35%, usefully from about 12% to about 20% by weight of the total weight of the composition, the DMSO solvent can comprise from about 59.9% to about 99.8%, usefully from about 79% to about 87% by weight of the total weight of the composition, and the therapeutic substance can comprise from about 0.1% to about 40%, usefully from about 1% to about 9% by weight of the total weight of the composition. More than 9% by weight of therapeutic substance can adversely affect characteristics that are desirable in the polymeric coating, such as adhesion of the coating to the prosthesis. Selection of a specific weight ratio of the ethylene vinyl alcohol copolymer and the DMSO solvent is dependent on factors such as the material from which the prosthesis is made, the geometrical structure of the prosthesis, and the type and amount of therapeutic substance employed.

In accordance with another embodiment, sufficient amounts of a therapeutic substance or combination of substances are dispersed in the blended composition of the ethylene vinyl alcohol copolymer, the DMSO solvent, and the wetting fluid. In this embodiment, the ethylene vinyl alcohol copolymer can comprise from about 0.1% to about 35%, usefully from about 10% to about 25% by weight of the total weight of the composition, the DMSO solvent can comprise from about 19.8% to about 98.8%, usefully from about 49% to about 79% by weight of the total weight of the composition, the wetting fluid can comprise from about 1% to about 80%, usefully from about 5% to about 40% by weight of the total weight of the composition, and the therapeutic substance can comprise from about 0.1% to about 40%, usefully from about 1% to about 9% by weight of the total weight of the composition. Selection of a specific weight ratio of the ethylene vinyl alcohol copolymer, the DMSO solvent, and the wetting fluid is dependent on factors such as the material from which the prosthesis is made, the geometrical structure of the prosthesis, and the type and amount of therapeutic substance employed.

The particular weight percentage of a therapeutic substance mixed within the composition, with or without the wetting fluid, depends on factors such as the type of therapeutic substance, duration of the release, cumulative amount of release, and release rate that is desired. It is known that the release rate and the cumulative amount of the therapeutic substance that is released is directly proportional to the total initial content of the substance in the copolymer's matrices. Accordingly, a wide spectrum of release rates can be achieved by modifying the ethylene comonomer content and the initial amount of substance. The therapeutic substance should be in true solution or saturated in the blended composition. If the therapeutic substance is not completely soluble in the composition, operations including mixing, stirring, and/or agitation can be employed to effect homogeneity of the residues. The therapeutic substance may be added so that dispersion is in fine particles. The mixing of the therapeutic substance can be conducted in an anhydrous atmosphere, at ambient pressure, and at room temperature such that supersaturating the therapeutic substance is not desired.

Exposure of the ethylene vinyl alcohol/DMSO composition or ethylene vinyl alcohol/DMSO/wetting fluid composition to the therapeutic substance is not permitted to adversely alter the substance's composition or characteristic. Accordingly, the particular therapeutic substance is selected for mutual compatibility with the blended composition. Therapeutic substances or agents can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analogue from Ibsen), angiotensin converting enzyme inhibitors such as Captopril® (available from Squibb), Cilazapril® (available from Hoffman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, and dexamethasone. While the foregoing therapeutic substances or agents are well known for their preventative and treatment properties, the substances or agents are provided by way of example and are not meant to be limiting. Other therapeutic substances which are currently available or may be developed are equally applicable for use with the present invention. The treatment of patients using the above mentioned medicines is well known to those of ordinary skill in the art.

Prosthesis

The prosthesis used in conjunction with the above-described composition may be any suitable prosthesis, examples of which include self-expandable stents, balloon-expandable stents, and grafts. The underlying structure of the prosthesis can be virtually any design. The prosthesis can be made of a metallic material or an alloy such as, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Prostheses made from bioabsorbable or biostable polymers could also be used with the blended composition. A polymeric prosthesis should be compatible with the composition. The ethylene vinyl alcohol copolymer, however, adheres very well to metallic materials, more specifically to stainless steel.

Methods for Coating the Prosthesis using the Composition

To form a coating on a surface of the prosthesis, the surface of the prosthesis should be clean and free from contaminants that may be introduced during manufacturing. However, the surface of the prosthesis requires no particular surface treatment to retain the applied coating. The composition can be applied to both the inner and outer (the tissue contacting) surfaces of the prosthesis. Application of the composition can be by any conventional method, such as by spraying the composition onto the prosthesis or immersing the prosthesis in the composition. The addition of a wetting fluid leads to a consistent application of the composition which causes the coating to be uniformly deposited on the surface of the prosthesis.

After the composition is applied, the prosthesis can be heating by, for example, passing the prosthesis over a hot plate. The prosthesis should be exposed to the heat for a short duration of time, typically about 3 to 5 seconds. The temperature of the hot plate can be from about 55° C. to about 65° C., typically about 60° C. Exposure of the prosthesis to the hot plate prevents the prosthesis from cooling at a rapid rate. Rapid cooling of the prosthesis may adversely affect properties that are generally desirable in a coating, such as elasticity. The polymer can be further exposed to heat treatment or cured for a predetermined duration of time, for example for about 6 hours. The heat treatment can be conducted generally at the same temperature range as the hot plate, for example from about 55° C. to about 65° C., typically about 60° C. The heat treatment prevents formation of air bubbles in the polymeric coating.

The DMSO solvent or the combination of the DMSO solvent and wetting fluid is removed from the composition on the surfaces of the prosthesis by allowing the DMSO solvent or combination of the DMSO solvent and wetting fluid to evaporate. The evaporation can be induced by heating the prosthesis at a predetermined temperature for a predetermined period of time. For example, the prosthesis can be heated at a temperature of about 60° C. to about 70° C. for about 12 hours to about 24 hours. The heating can be conducted in an anhydrous atmosphere and at ambient pressure. The heating can, alternatively, be conducted under a vacuum condition. It is understood that essentially all of the DMSO solvent and the wetting fluid will be removed from the composition but traces or residues can remain blended with the copolymer.

Coating

In one embodiment, the coating comprises a polymeric material made from essentially an ethylene vinyl alcohol copolymer. The ethylene vinyl alcohol copolymer can serve as a primer for allowing substances, such as a variety of polymeric materials, to be easily and effectively secured by a prosthesis, more particularly a prosthesis made from a metallic material such as stainless steel.

The ethylene vinyl alcohol copolymer can serve as an under-layer for a heparin coating for the prosthesis, allowing the heparin coating to be secured more easily and effectively by the prosthesis. The heparin coating can be formed on the ethylene vinyl alcohol copolymer coating by any conventional method such as immersion or spraying techniques as is understood by one of ordinary skill in the art.

The ethylene vinyl alcohol copolymer is a biocompatible coating, i.e., a coating which, in the amounts employed, is non-toxic, non-inflammatory, chemically inert, and substantially non-immunogenetic. By way of example, and not limitation, the coating can have a thickness of about 0.5 microns to about 2.0 microns. The particular thickness of the layer is dependent on the desired use of the primer and the type of procedure for which the prosthesis is employed.

In another embodiment, the coating comprises a polymeric material made from essentially an ethylene vinyl alcohol copolymer having a therapeutic substance or a combination of substances impregnated therein. The inclusion of the therapeutic substance or substances in the matrices of the copolymer allows not only retention of the substance on the prosthesis (e.g., a stent) during delivery and, if applicable, expansion of the prosthesis, but also controlled administration of the substance following implantation. By way of example, and not limitation, the impregnated ethylene vinyl alcohol copolymer can have a thickness of about 0.5 microns to about 1.5 microns. The particular thickness of the copolymer is based on the type of procedure for which prosthesis is employed and the amount of therapeutic substance that is desired to be delivered. The amount of therapeutic substance to be included on the prosthesis can be further increased by applying a plurality of coating layers onto the prosthesis. The application of each layer should be performed subsequent to the evaporation of the DMSO solvent or DMSO/wetting fluid and the drying of the copolymer of the previous layer.

In one embodiment, a layer or a second coating formed from a polymeric material, without a therapeutic substance, is deposited on the therapeutic substance impregnated copolymer coating. Suitable polymeric material can include, but are not limited to, polycaprolactone (PCL), poly-D,L-lactic acid (DL-PLA), poly-L-lactic acid (L-PLA), poly (lactide-co-glycolide), poly(hydroxybutyrate), poly (hydroxybutyrate-co-valerate), polydioxanone, polyorthoester, polyanhydride, poly(glycolic acid), poly (glycolic acid-cotrimethylene carbonate), polyphosphoester, polyphosphoester urethane, poly (amino acids), cyanoacrylates, poly(trimethylene carbonate), poly (iminocarbonate), copoly(ether-esters), polyalkylene oxalates, polyphosphazenes, polyiminocarbonates, and aliphatic polycarbonates, fibrin, fibrinogen, cellulose, starch, collagen, Parylene®, Parylast®, polyurethane, polyethylene, polyethylene teraphthalate, ethylene vinyl acetate, silicone, polyethylene oxide, and mixtures thereof.

In another embodiment, a layer or a second coating formed from essentially an ethylene vinyl alcohol copolymer, without a therapeutic substance, can be deposited on the therapeutic substance impregnated copolymer coating. The substance-free ethylene vinyl alcohol copolymer used as a second coating can comprise a mole percent of ethylene of from about 27% to about 44%. It is understood by one of ordinary skill in the art that ethylene vinyl alcohol copolymer may also be a terpolymer so as to include small amounts of additionally monomers, for example less than about five (5) mole percentage of styrenes, propylene, and other suitable monomers.

The second coating produces a membrane that reduces the rate of release of the therapeutic substance or substances from the impregnated ethylene vinyl alcohol copolymer, particularly therapeutic substances that are water soluble (e.g., heparin, rapamycin, and dexamethasone). If an ethylene vinyl alcohol copolymer is used as a rate reducing membrane, as a general rule, an increase in the amount of ethylene comonomer content of the second coating decreases the rate that a therapeutic substance can permeate through the matrices of the second coating. By way of example, and not limitation, the second coating can have a thickness of about 0.25 microns to about 1.5 microns. Typically, the second coating can have a thickness of about 1 micron. It is understood by one of ordinary skill in the art that the thickness of the layer is based on factors such as the type of procedure for which the prosthesis is employed and the rate of release that is desired.

Method of Use

In accordance with the above described method, therapeutic substances can be applied to a prosthesis, e.g., a stent, retained on the stent during delivery and expansion of the stent, and released at a desired control rate and for a predetermined duration of time at the site of implantation. The release rate of the substances can be controlled by modifying release parameters such as the amount of ethylene comonomer content of the copolymer and the initial therapeutic substance content in the matrices of the copolymer. Correlations and interrelations between release parameters are well known by one of ordinary skill in the art. The rate of release can also be adjusted by the addition of second polymeric layer, with or without a therapeutic substance. A stent having the above described medicated coating is useful for a variety of medical procedures, including, by way of example, treatment of obstructions caused by tumors in bile ducts, esophagus, and trachea/bronchi. A stent having the above described medicated coating is particularly useful for treating occluded regions of blood vessels caused by formation of intimal flaps or torn arterial linings, thrombosis, and restenosis. Stents may be placed in a wide array of blood vessels, both arteries and veins. Representative examples of sites include the iliac, renal, and coronary arteries.

Briefly, an angiography is first performed to determine the appropriate positioning for stent therapy. Angiography is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters such as, grams of ethylene vinyl alcohol copolymer, DMSO, wetting fluid, and therapeutic substance, temperature, duration of time, thickness of coating, and all other parameters and data are not be construed to unduly limit the scope of the embodiments of the invention.

Example 1

Multi-Link™ stents (available from Guidant Corporation) were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. The mixture was placed in a warm water shaker bath at 60° C. for 24 hours. The solution was cooled and vortexed. The cleaned Multi-Link™ stents were dipped in the EVOH solution and then passed over a hot plate, for about 3–5 seconds, with a temperature setting of about 60° C. The coated stents were heated for 6 hours in an air box and then placed in a oven at 60° C., under vacuum condition, and for 24 hours. The coated stents were expanded on a 4.0 mm angioplasty balloon. The coatings remained intact on the stents. The coatings were transparent giving the Multi-Link™ stents a glossy-like shine.

Example 2

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 4 grams of DMSO, making an EVOH:DMSO ratio of 1:4. Dexamethasone was added to the 1:4 EVOH:DMSO solution. Dexamethasone constituted 9% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box and then placed in a vacuum oven at 60° C. for 24 hours. The above-recited step was repeated twice. The average weight of the coating was 0.0003 grams, having an estimated dexamethasone content of 75 ug per stent. The coated stents were expanded on a 4.0 mm angioplasty balloon. The coatings remained intact on the stents. Verification of coverage and physical properties of the coatings were visualized using a scanning electron microscope. The coatings were transparent, giving the Multi-Link™ stents a glossy-like shine.

Example 3

Multi-Link Duet™ stents are cleaned by placement in an ultrasonic bath of isopropyl alcohol solution for 10 minutes. The stents are dried and plasma cleaned in a plasma chamber. The EVOH solution is made with 1 gram of EVOH and 4 grams of DMSO, making an EVOH:DMSO ratio of 1:4. Dexamethasone is added to the 1:4 EVOH:DMSO solution. Dexamethasone constitutes 9% by weight of the total weight of the solution. The solution is vortexed and placed in a tube. The cleaned Multi-Link™ stents are attached to mandrel wires and dipped into the solution. The coated stents are passed over a hot plate, for about 3–5 seconds, with a temperature setting of about 60° C. The coated stents are cured for 6 hours in an air box then placed in a vacuum oven at 60° C. for 24 hours. The single layered dexamethasone/EVOH coated stents are dipped into the 1:4 ratio EVOH:DMSO solution, free from dexamethasone. The stents are passed over the hot plate, cured, and placed in the oven as previously described. The top coating will provide a barrier layer for controlling the release of dexamethasone from the drug coated layer. The coated stents can be expanded on a 4.0 mm angioplasty balloon. It is predicted that the coatings will remain intact on the stents. The coatings will be transparent, giving the Multi-Link™ stents a glossy-like shine.

Example 4

Figure 2:
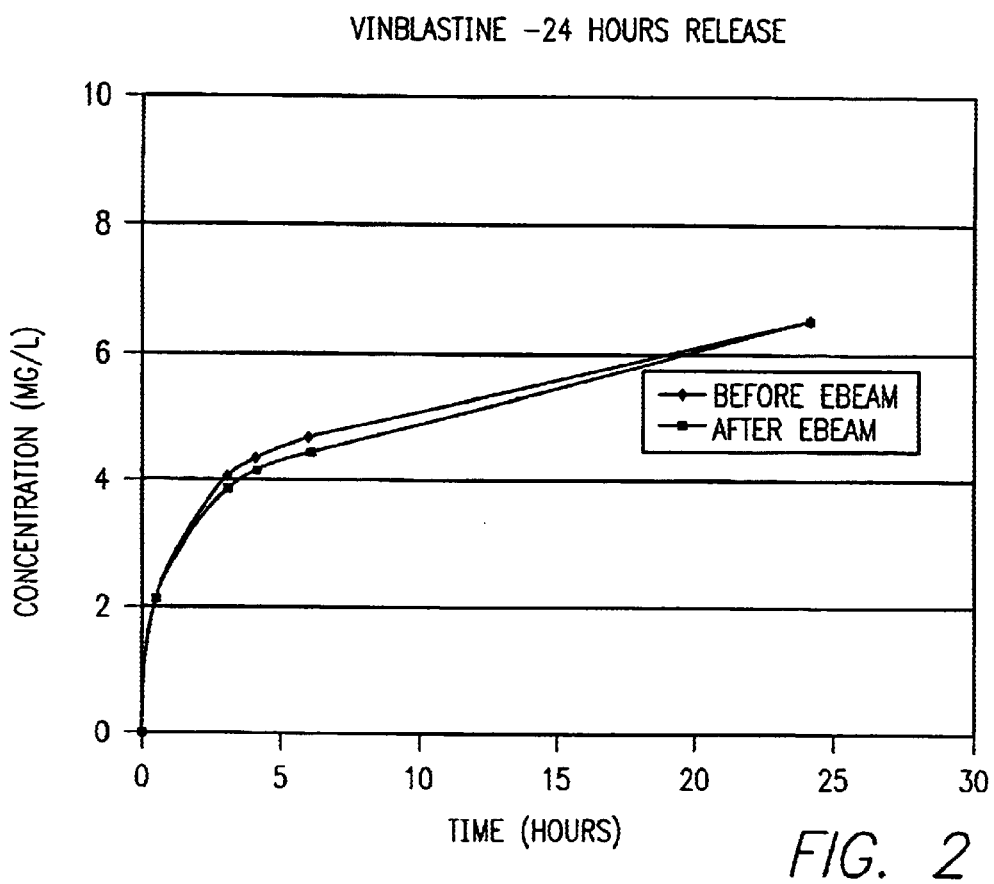
FIG. 2 is a plot showing elution profiles for stents with a coating of ethylene vinyl alcohol copolymer impregnated with vinblastine made according to Example 4.

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Vinblastine was added to the 1:7 EVOH:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 grams, with an estimated vinblastine concentration of 12 ug per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 2. The data indicates that electron beam radiation procedure does not interfere in the release of vinblastine from EVOH.

| Release Profile For Vinblastine -- Unsterilized | | | |
| --- | --- | --- | --- |
| Time (Hours) | uG Released | Total uG Released | uG Release per Hour |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |
| 6 | 0.38 | 4.68 | 0.19 |
| 24 | 1.7 | 6.38 | 0.09 |

| Release Profile For Vinblastine -- Sterilized | | | |
| --- | --- | --- | --- |
| Time (Hours) | uG Released | Total uG Released | uG Release per Hour |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 5

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Cephalotaxin was added to the 1:7 EVO- H:DMSO solution. Cephalotaxin constituted 5% by weight of the total weight of the solution. The solution was vortexed and placed in a tube. The cleaned Multi-Link™ stents were attached to mandrel wires and dipped into the solution. The coated stents were passed over a hot plate, for about 3–5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00013 grams, with an estimated cephalotaxin concentration of 33 ug. The stents were sterilized by electron beam radiation. Cephalotaxin/EVOH coated stents and EVOH-coated control stents were implanted in the coronary arteries of 4 pigs, generally in accordance to the procedure set forth in "Restenosis After Balloon Angioplasty-A Practical Proliferative Model in Porcine Coronary Arteries" by Robert S. Schwartz, et al., Circulation 82(6):2190–2200, December 1990, and "Restenosis and the Proportional Neointimal Response to Coronary Artery Injury: Results in a Porcine Model" by Robert S. Schwartz et al, J Am Coll Cardiol; 19:267–74 February 1992. Results of the porcine artery study indicated that there was no significant difference between the uncoated, EVOH coated and cephalotaxin coated stents in the amount of neointimal proliferation resulting from arterial injury.

Example 6

Multi-Link Duet™ stents (available from Guidant Corporation) were cleaned by placement in an ultrasonic bath of isopropryl alcohol solution for 20 minutes, then air dried. An EVOH stock solution was made with 1 gram of EVOH and 7 grams of DMSO, making an EVOH:DMSO ratio of 1:7. The mixture was placed in a warm water shaker bath at 60° C. for 12 hours. The solution was mixed, then cooled to room temperature. A co-solvent was added to the EVOH solution to promote wetting of the struts of the Multi-Link Duet™ stents. One gram of tetrahydrofuran (THF) was mixed with 1.2 grams of the EVOH:DMSO solution. The cleaned Multi-Link Duet™ stents were attached to mandrel wires and dipped into the solution. The coated stents were passed over a hot plate, for about 3 to 5 seconds, with a temperature setting of about 60° C. The coated stents were then heated in a laboratory oven at 90° C. for 4 hours. The thin EVOH coating adhered to stainless steel without peeling or cracking. EVOH forms a superior primer base coat for other polymers that do not adhere well to stainless steel.

Example 7

Multi-Link Duet™ stents were cleaned in an ultrasonic bath of isopropyl alcohol for 20 minutes, then air dried. An EVOH solution was made with 1 gram of EVOH and 5 grams of DMSO, making an EVOH:DMSO ratio of 1:5. The mixture was placed in a warm water shaker bath at 60° C. for 12 hours. The solution was mixed, then cooled to room temperature. The dissolved EVOH:DMSO solution was mixed with 24.6 grams of THF and 19.56 grams of DMSO. The solution was mixed then placed in the reservoir of an air pressured atomizing sprayer. Multi-Link Duet™ stents were sprayed while the stents rotated between 30 to 120 rpm. The spray time was dependent upon the flow rate of the sprayer. A flow rate between 1 to 20 mg/second required a stent to be sprayed between 1 to 30 seconds. The polymer coated Multi-Link Duet™ stents were heated in a forced air convection oven for 12 hours. The coatings were transparent, giving the Multi-Link Duet™ stents a glossy-like shine.

Example 8

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. Various co-solvents were examined to determine which co-solvent would promote a thicker coating. These co-solvents were THF, DMF, 1-butanol, and n-butyl acetate. The formulation for the co-solvents was as follows. Three grams of dissolved EVOH:DMSO solution was mixed with 0.9 grams of THF; three grams of dissolved EVOH:DMSO solution was mixed with 0.39 grams of DMF; three grams of dissolved EVOH:DMSO solution was mixed with 0.5 grams of 1-butanol; and three grams of dissolved EVOH:DMSO solution was mixed with 0.68 grams of n-butyl acetate. The cleaned Multi-Link Duet™ stents, attached to mandrel wires, were dipped into the solutions. The coated stents were passed over a hot plate, for about 3 to 5 seconds, with a temperature setting of about 60° C. The coated stents were heated in a forced air convection oven for 24 hours. A second layer of coating was applied to coated Multi-Link Duet™ stents and the stents were heated in the same manner as above. No difference was seen between the stents coated with the various co-solvents (e.g., greater weight of coating or physical appearance). All coated stents were transparent, giving the Multi-Link Duet™ stents a glossy-like shine. No webbing or bridging of the coating was seen between the struts of the coated Multi-Link Duet™ stents. The weight of the coatings was between 0.2 to 0.27 mg/stent.

Example 9

Multi-Link Duet™ stents are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVOH:DMSO solution is mixed with 0.29 grams of Dexamethasone, then 0.9 grams of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A coating for a stent, comprising a first layer and a second layer disposed over the first layer, wherein the first layer comprises an ethylene-vinyl alcohol copolymer and a therapeutic substance and the second layer comprises an ethylene-vinyl alcohol copolymer, the second layer being free from any therapeutic substances.

2. The coating of claim 1, wherein the therapeutic substance is water soluble.

3. The coating of claim 1, wherein the therapeutic substance is for the treatment of restenosis.

4. The coating of claim 1, wherein the second layers is for reducing the rate of release of the therapeutic substance from the coating.

5. The coating of claim 1, wherein the second layer is the outermost layer of the coating.

6. A coating for a stent, the coating comprising a first polymeric region comprising an ethylene-vinyl alcohol copolymer and a therapeutic substance and a second polymeric region free from any therapeutic substances disposed over the first polymeric region, the second polymeric region comprising an ethylene-vinyl alcohol copolymer.

7. The coating of claim 6, wherein the coating additionally comprises heparin.

8. The coating of claim 6, wherein the stent is balloon expandable or self-expandable.

9. The coating of claim 6, wherein the therapeutic substance is water soluble.

10. The coating of claim 6, wherein the therapeutic substance is for the treatment of restenosis.

11. A coating for a stent, comprising a first layer and a second layer, wherein the first layer includes a therapeutic substance and the second layer includes an ethylene-vinyl alcohol copolymer and is free from any therapeutic substances.

12. The coating of claim 11, wherein the second layer is disposed over the first layer.

13. A prosthesis comprising a coating for delivery of a drug, wherein the coating includes:
   (a) a reservoir layer of a drug; and
   (b) a rate-reducing layer disposed over the reservoir layer for reducing the rate of release of the drug from the coating, the rate reducing layer being free from any drugs and comprising an ethylene vinyl alcohol copolymer.

14. The prosthesis of claim 13, wherein the reservoir layer additionally comprises an ethylene-vinyl alcohol copolymer.

15. The prosthesis of claim 13, wherein the prosthesis is a balloon expandable or self-expandable stent.

16. A prosthesis comprising a coating for delivery of a drug, wherein the coating includes:
   (a) a first region comprising a polymer and a drug; and
   (b) a second region disposed over the first region, the second region comprising an ethylene-vinyl alcohol copolymer for reducing the rate of release of the drug from the coating.

17. The prosthesis of claim 16, wherein the drug is water soluble.

18. The prosthesis of claim 16, wherein the prosthesis is a balloon expandable stent or self-expandable stent.

19. The prosthesis of claim 16, wherein the polymer of the first region is an ethylene-vinyl alcohol copolymer.

20. A method for coating a stent, comprising:
   forming a first layer comprising a polymer and a drug; and
   forming a second layer over the first layer, the second layer comprising an ethylene-vinyl alcohol copolymer and being free from any drugs.

21. The method of claim 20, wherein the polymer of the first layer comprises an ethylene-vinyl alcohol copolymer.

22. The method of claim 20, wherein the drug is for the treatment of restenosis.

23. A method for coating a stent, comprising:
   applying a first composition to the stent, the first composition comprising a polymer and a drug;
   allowing the polymer to solidify to form a polymeric layer containing the drug; and
   applying a second composition free from any drugs to the solidified polymeric layer, the second composition comprising an ethylene-vinyl alcohol copolymer.

24. The method of claim 23, wherein the application of the first or second composition can be conducted by spraying.

25. The method of claim 23, wherein the first composition additionally comprises a solvent, and wherein the allowance of the polymer to solidify comprises allowing the solvent to evaporate from the composition.

26. The method of claim 23, wherein the polymer of the first composition comprises an ethylene-vinyl alcohol copolymer.

27. The method of claim 23, wherein the first composition or second composition additionally comprises a fluid having a contact angle of less than 90°.

28. The method of claim 23, wherein the first composition or second composition additionally comprises a fluid selected from the group consisting of dimethylsulfoxide, tetrahydrofuran, dimethylformamide, 1-butanol, n-butyl acetate, or mixtures thereof.

29. The method of claim 23, wherein the second composition additionally comprises a fluid selected from the group consisting of dimethylsulfoxide, tetrahydrofuran, dimethylformamide, 1-butanol, n-butyl acetate, or mixtures thereof and wherein the method additionally comprises allowing the fluid to evaporate from the composition.

* * * * *

UNITED STATES PATENT AND TRADEMARK OFFICE
CERTIFICATE OF CORRECTION

PATENT NO. : 6,713,119 B2
DATED : March 30, 2004
INVENTOR(S) : Hossainy et al.

It is certified that error appears in the above-identified patent and that said Letters Patent is hereby corrected as shown below:

Column 1,
Line 10, change "Pat. No. 6,719,381" to -- Pat. 6,379,381 --.

Column 15,
Line 3, change "second layers" to -- second layer --.

Column 16,
Line 42, change "or mixtures thereof" to -- and mixtures thereof --.
Lines 46-47, change "or mixtures thereof and" to -- and mixtures thereof, and --.

Signed and Sealed this

Twenty-seventh Day of July, 2004

JON W. DUDAS
*Acting Director of the United States Patent and Trademark Office*